United States Patent [19]

Lane

[11] Patent Number: 4,924,712
[45] Date of Patent: May 15, 1990

[54] REACTION TIME DISPLAY DEVICE

[76] Inventor: John M. Lane, 12665 Fiori La., Sebastopol, Calif. 95472

[21] Appl. No.: 361,329

[22] Filed: Jun. 5, 1989

[51] Int. Cl.$^5$ ............................................. A63B 67/00
[52] U.S. Cl. ................................................. 73/865.4
[58] Field of Search ................... 73/865.4; 273/1 GE, 273/85 C

[56] References Cited

U.S. PATENT DOCUMENTS 2,834,597  5/1958  Ylinen ............................ 273/1 GE
3,970,303  7/1976  Levering ........................ 273/1 GE Primary Examiner—Robert Raevis

[57] ABSTRACT

The invention provides a simple device to determine reaction time.

1 Claim, 1 Drawing Sheet

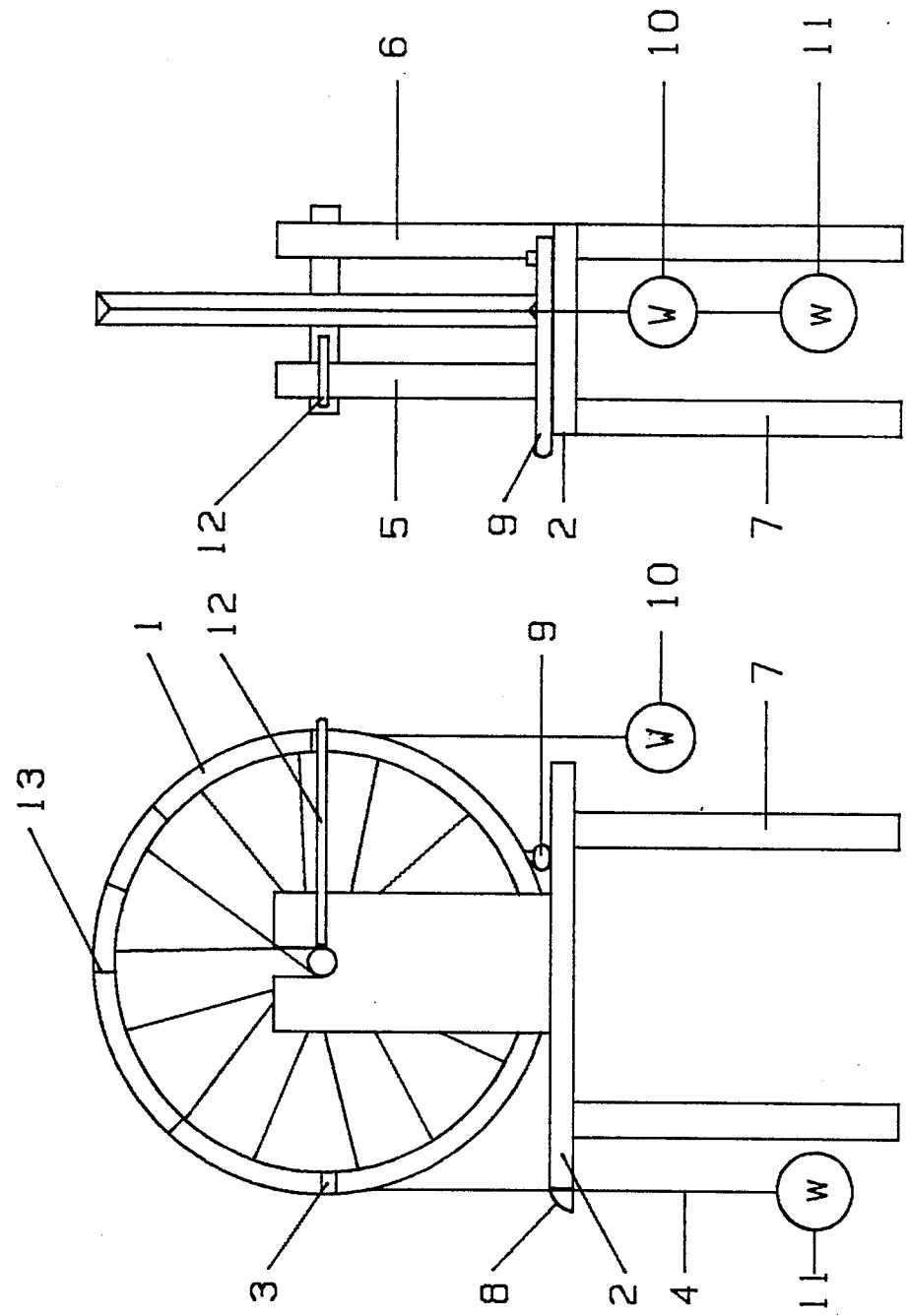

REACTION TIME DISPLAY DEVICE

BACKGROUND OF THE INVENTION

The Present State of the Art and Field of Invention

There appears to be no prior device known to measure reaction time. This invention is the only device known to measure reaction time now available. During World War II reaction time was measured by using two blank shotgun shells mounted under a vehicle to fire at will. When the vehicle reached the speed of 20 MPH the operator would discharge his gun. The driver being tested then stepped on the brake as quickly as possible, causing the second shot to be fired on the pavement. The distance between the two powder marks was measured and converted to fractions of a second for the reaction time. The field of application of this device could be extensive. Coaches, athletes, sporting centers, health centers, and schools could make good use of it. Because of heavily traveled highways it is possible the State Departments of Motor Vehicles could well use it for driver reaction time.

SUMMARY OF THE INVENTION

This invention consists of a simple device to determine personal reaction time. Reaction time measurement could be of great benefit to Health Clubs, Sport Clubs and to Coaches and other Directors of athletic training. Reaction time changes could be an excellent indicator of condition of patients in Clinics or Hospitals.

Reaction time might be of great importance in this world of overcrowded streets and freeways. It could be practical as a basis for drivers licenses to Departments of Motor Vehicles in each State.

The Device is inexpensive, requires no external source of power, either electrical or mechanical to operate, hence requires little or no maintenance, and it can be set up and used almost anywhere.

BRIEF DESCRIPTION OF THE DRAWING

The drawing showing a front view (FIG. 1) and side view (FIG. No. 2) of the Reaction Time Display Device wherein the various parts are designated by numerals except the weights which designated by (w) and (W).

The reaction time display device as set forth in these specifications requires certain technical determinations for the satisfactory operation of this device.

Distance of fall of the heavier weight is limited to less than four convenient operation. Reaction time display of ¾ second or less is determined to be adequate. Distance of all under normal gravity in ¾ second is 9 feet. By reducing gravity to ⅓ the distance of all is 3 feet. This is considered satisfactory for the operation of this device.

Using the new gravity at ⅓, this figure is entered into the formula established by Professor Atwood in his study of he effect of unequal weights on gravity, it was determined the ratio is 2:1, thus the heavier weight must be twice that of the smaller.

The following entrees of time and distance of fall are entered as shown below on the rim of the wheel:

| time | distance | time | distance |
| --- | --- | --- | --- |
| ⅛ | 1" | ½ sec | 16" |
| 3/16" | 2¼" | 9/16" | 20¼" |
| ¼" | 4" | ⅝" | 25" |
| 5/16" | 6¼" | 11/16" | 30¼" |
| ⅜" | 9" | ¾" | 36" |
| 7/16" | 12¼" | ¾" | 36" |

The requirement of four foot separation between applicant and device is arbitrary but necessary for standardization.

DETAILED WRITTEN DESCRIPTION

The device consists of a frictionless wheel (1) mounted on a support base (2) with weights uprights (5) and (6) to contain the axle of the wheel in such a manner that the wheel (1) will turn freely, allowing the weights (w) and (W), secured at opposite ends of the card (b), equidistant from and anchored at the valve stem hole ( ) to rise and fall freely.

The support base (2) will be mounted a stand (7) of sufficient height to allow the (W) a free fall of at three feet. Uprights (5) and (6) to be notched to allow easy removal of the wheel.

Elements (8) and (9) are locations of braking devices of any sort. Elements (10) and (11) also indicate the weights. FIG. (12) shows a horizontal pointer to indicate where zero reading is. The markings as indicated by FIG. (13) i.e. present the various fractions of a second on the rim when the wheel is stopped.

This invention pertains to a mechanical device designed to measure human reaction time. The device consists of two unequal weights suspended over a frictionless wheel by a suitable cord and set up in such a fashion that the weights are free to move up and down as the wheel turns. The wheel to be mounted vertically in a rigid frame placed on a stand or tripod, of suitable height for operation. The cord connecting the two weights to be anchored at one point on the wheel so that they are equidistant from this point. Each side being 40" in length to provide clearance from the wheel. To perform the test the applicant stands at a predetermined distance in front of the wheel with his eyes focused on the heavier weight. As the weights are released by the operator, the participant stops the wheel as quickly as possible by applying the brake. The mark on the wheel at the horizontal level will indicate the reaction time.

I claim:

1. A device to measure the reaction time of an individual, comprising:
 a base; a freely rotatable wheel rotatable about a horizontal axis supported by the base, said wheel having indicia positioned on the rim of the wheel said indicia representative of fractions of a second; a cord means attached to the rim of the wheel at the midsection of the cord means, said cord means contacting the rim of the wheel along the circumference of at least the top half of the wheel, and having two ends, each end extending vertically downward below the horizontal axis; a first weight attached to one end of the cord means to apply a rotational force to the wheel in one direction, and a second heavier weight attached to the second end of the cord means to apply a greater rotational force to the wheel in a direction opposite to the first direction; braking means operable to stop wheel rotation; and a pointer operatively coupled to the base, and operably associated with the indicia to provide a reaction time value; whereby when the weights are released from a starting static position by an operator, the individual stops the rotation of the wheel as quickly as possible by applying the braking means, whereby the pointer and indicia provide a reaction time value.

* * * * *